United States Patent
Storzum et al.

(10) Patent No.: US 7,291,748 B2
(45) Date of Patent: Nov. 6, 2007

(54) C10/C7 ESTER MIXTURES BASED ON 2-PROPYLHEPTANOL

(75) Inventors: Uwe Storzum, Worms (DE); Boris Breitscheidel, Limburgerhof (DE); Peter Schwab, East Hanover, NJ (US); Patrick Harmon, Houston, TX (US); David P. Owen, Dearborn, MI (US)

(73) Assignee: BASF Corporation, Florham Park, NJ (US)

( * ) Notice: Subject to any disclaimer, the term of this patent is extended or adjusted under 35 U.S.C. 154(b) by 42 days.

(21) Appl. No.: 11/191,227

(22) Filed: Jul. 28, 2005

(65) Prior Publication Data

US 2007/0027242 A1 Feb. 1, 2007

(51) Int. Cl.
*C07C 69/80* (2006.01)
*C07C 69/82* (2006.01)

(52) U.S. Cl. .......................................... 560/76; 560/103

(58) Field of Classification Search ...................... None
See application file for complete search history.

(56) References Cited

U.S. PATENT DOCUMENTS

| | | | |
|---|---|---|---|
| 2,921,089 A | 1/1960 | Hagemeyer et al. | |
| 4,426,542 A | 1/1984 | Barker et al. | |
| 5,324,853 A | 6/1994 | Jones et al. | |
| 5,434,313 A | 7/1995 | Harrison et al. | |
| 6,310,235 B1 | 10/2001 | Gick | |
| 6,482,972 B1 * | 11/2002 | Bahrmann et al. | 560/76 |

FOREIGN PATENT DOCUMENTS

| | | |
|---|---|---|
| DE | A 1 945 359 | 8/1969 |
| DE | A 2 612 355 | 3/1976 |
| EP | A 155 508 | 9/1985 |
| EP | A 213 639 | 3/1987 |
| EP | 366 089 B1 | 6/1994 |
| JP | 4 104 740 | 4/1992 |
| JP | 4 106 132 | 4/1992 |
| JP | 4 106 145 | 4/1992 |
| JP | 4 106 146 | 4/1992 |
| JP | 4 258 641 | 9/1992 |
| JP | 4 299 924 | 10/1992 |
| JP | 5 194 761 | 8/1993 |
| JP | 5 194 810 | 8/1993 |
| JP | 5 214 159 | 8/1993 |
| JP | 5 214 192 | 8/1993 |
| JP | 5 339 388 | 12/1993 |
| JP | 6 001 858 | 1/1994 |
| JP | 6 001 862 | 1/1994 |
| JP | 6 001 900 | 1/1994 |
| JP | 6 001 901 | 1/1994 |
| JP | 6 002 281 | 1/1994 |
| JP | 7 157 615 | 6/1995 |
| JP | 7 173 356 | 7/1995 |
| JP | 7 179 699 | 7/1995 |
| JP | 7 304 920 | 11/1995 |
| JP | 7 304 921 | 11/1995 |
| JP | 7 304 922 | 11/1995 |
| JP | 8 003 401 | 1/1996 |
| JP | 8 034 891 | 2/1996 |
| JP | 8 059 937 | 3/1996 |
| JP | 8 157 422 | 6/1996 |
| JP | 8 283 510 | 10/1996 |
| JP | 8 301 295 | 11/1996 |
| WO | WO 02/38531 | 5/2002 |
| WO | WO 02/083695 | 10/2002 |

OTHER PUBLICATIONS

Palatinol 7PHP technical data sheet. Aug. 2004.*
Technical Data Sheet Palatinol 7PHP General Purpose PHTHALATE in Aug. 2004.
Kirk-Othmer; Encyclopedia of Chemical Technology; vol. 17; pp. 843-854; John Wiley & Sons; New York 1996
Towae et al. in Ullmann's Encyclopedia of Industrial Chemistry, 5th Ed., vol. A20, pp. 193-196, VCH Publishers, Weinheim 1992.
Kirk-Othmer; Encyclopedia of Chemical Technology, 4th Ed., vol. 24, pp. 1017-1047; John Wiley & Sons; New York 1996.
L. Meier in R. Gachter, H. Muller (Ed.); Plastics Additives Handbook, 3rd E., Chapters 5.4.3, 5.4.4., Hanser Publishers, Munich 1990.
Testing of Plastics, Determination of Solubility Temperature of Polyvinyl Chloride (PVC) in Plasticizers, DIN 53408, Berlin, Jun. 1967.

* cited by examiner

*Primary Examiner*—Yvonne Eyler
*Assistant Examiner*—Yevgeny Valenrod
(74) *Attorney, Agent, or Firm*—Cheng Q. Song; Brian W. Stegman

(57) ABSTRACT

Ester mixture comprising at least one ester of an aliphatic or aromatic di- or tricarboxylic acid having a $C_{10}$ alcohol component composed of 2-propylheptanol or composed of a $C_{10}$ alcohol mixture composed of 2-propylheptanol and of at least one of the $C_{10}$ alcohols 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol, and comprising at least one ester of an aliphatic or aromatic di- or tricarboxylic acid having a $C_7$ alcohol component composed of n-heptanol or composed of an alcohol mixture composed of n-heptanol with at least one of the $C_7$ alcohols 2-methylhexanol and/or 2-ethylpentanol, where the aliphatic or aromatic di- or tricarboxylic acid has been selected from the group consisting of citric acid, phthalic acid, isophthalic acid, terephthalic acid, and trimellitic acid, and polyvinyl chloride composition comprising this ester mixture.

9 Claims, No Drawings

C10/C7 ESTER MIXTURES BASED ON 2-PROPYLHEPTANOL

FIELD OF THE INVENTION

The present invention relates to an ester mixture comprising at least one ester of an aliphatic or aromatic di- or tricarboxylic acid having a $C_{10}$ alcohol component composed of 2-propylheptanol or composed of an alcohol mixture composed of 2-propylheptanol and of at least one of the $C_{10}$ alcohols 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol, and comprising at least one ester of an aliphatic or aromatic di- or tricarboxylic acid having a $C_7$ alcohol component composed of n-heptanol or composed of an alcohol mixture composed of n-heptanol with at least one of the $C_7$ alcohols 2-methylhexanol and/or 2-ethylpentanol, where the aliphatic or aromatic di- or tricarboxylic acid has been selected from the group consisting of citric acid, phthalic acid, isophthalic acid, terephthalic acid, and trimellitic acid, and to a polyvinyl chloride composition comprising this ester mixture.

BACKGROUND

U.S. Pat. No. 2,921,089 describes the use of dipropylheptyl phthalate and dipropylheptyl adipate as plasticizers for polyvinyl chloride (PVC) and cellulose acetate. The mixtures of these esters with PVC are said to feature good low-temperature flexibility properties.

U.S. Pat. No. 4,426,542 teaches the preparation of alcohol mixtures which comprise 2-propylheptanol and 2-propyl-4-methylhexanol, the use of these alcohol mixtures for the preparation of phthalic esters, and the use of these phthalic esters as plasticizers for PVC. The mixtures of these esters with PVC are said to have good low-temperature flexibility properties and low plasticizer volatility.

EP 366 089 discloses the preparation of alcohol mixtures which comprise 2-propylheptanol and other isomeric $C_{10}$ alcohols, the use of these alcohol mixtures for the preparation of phthalic esters, and the use of these phthalic esters as plasticizers for PVC. The mixtures of these esters with PVC are said to have high electrical resistivity. They are moreover said to feature low plasticizer volatility and high resistance to kerosine-extraction of the plasticizer.

JP 4 104 740, JP 4 106 132. and JP 4 106 145 describe PVC foils with dipropylheptyl phthalate as plasticizer. These foils are said in particular to have good mechanical properties and to be capable of use in the agricultural sector and also in the construction sector.

JP 4 106 146 discloses plasticized PVC compositions with dipropylheptyl phthalate as plasticizer, where the plasticizer has low volatility and high resistance to oil-extraction, and the compositions can be used as cable sheathing.

The subject matter of JP 4 299 924 is PVC coatings for acrylic polymers with dipropylheptyl phthalate as plasticizer, these being resistant to soiling and capable of use in the agricultural sector.

According to JP 4 258 641, PVC coatings with dipropylheptyl phthalate and epoxidized 1,2-polybutadiene as plasticizer feature very good weathering resistance.

JP 5 194 761 and JP 5 194 810 relate to the production of coatings from PVC and phthalic esters which can be prepared from alcohol mixtures comprising 2-propylheptanol and 2-propyl-4-methylhexanol. The coatings are said to resist soiling and to be water-resistant.

JP 5 214 159 and JP 5 214 192 concern compositions composed of PVC and of plasticizer esters which can be prepared from alcohol mixtures comprising 2-propylheptanol, 2-propyl-4-methylhexanol, and 2-methyl-2-ethylheptanol. The compositions are said to be relatively resistant to oil and to water and to have only a slight tendency toward plasticizer exudation.

JP 5 339 388 and JP 6 002 281 describe PVC foils and PVC synthetic leather which comprise phthalates whose preparation was based on alcohol mixtures composed of 2-propylheptanol and 2-propyl-4-methylhexanol. The good low-temperature flexibility properties of these PVC foils are emphasized in that specification.

JP 6 001 858, JP 6 001 862, JP 6 001 900, and JP 6 001 901 describe plasticized PVC compositions with phthalates whose preparation was based on alcohol mixtures composed of 2-propylheptanol and 2-propyl-4-methylhexanol. These compositions can be used for the coating of umbrellas, tents, or rainproof jackets, for cable sheathing, and also for the production of interior trim for buildings and automobiles.

JP 7 157 615 discloses plasticized PVC compositions with plasticizer mixtures which comprise esters based on the alcohols 2-propylheptanol and 2-propyl-4-methylhexanol. Alongside the good low-temperature flexibility properties of these compositions, mention is made of the low volatility of the plasticizer in these compositions.

JP 7 173 356 describes plasticized PVC compositions with phthalates based on the alcohols 2-propylheptanol and 2-propyl-4-methylhexanol, with high electrical resistance, which can be used as cable sheathing.

JP 7 179 699, JP 8 034 891, JP 8 059 937, and JP 8 283 510 relate to plasticized PVC coatings with phthalates based on the alcohols 2-propylheptanol and 2-propyl-4-methylhexanol, which can be used for the production of floorcoverings, interior decoration, baby pants, shower curtains, and also printed packaging foils.

JP 8 157 422 describes phthalic esters with mixtures composed of aliphatic $C_9$, $C_{10}$, and $C_{11}$ alcohols in which the alcohols present comprise 2-propylheptanol and 2-propyl-4-methylhexanol, and their use as plasticizers for the production of compounded plasticized PVC materials with good stability at high and low temperatures.

JP 8 301 295 describes plasticized PVC foils with esters based on the alcohols 2-propylheptanol and 2-propyl-4-methylhexanol, and their use for the production of flexible containers for the transport of synthetic resins.

JP 7 304 920, JP 7 304 921, JP 7 304 922, and JP 8 003 401 disclose plasticized PVC pastes with dipropylheptyl phthalate which feature good storage stability and can be used as plastisols, for example in the production of sealing compositions for the automotive industry.

Since August 2004, the applicant has been offering for sale the product Palatinol® 7PHP in the USA, this being a plasticizer mixture composed mainly of linear diheptyl phthalate and dipropylheptyl phthalate, and in this connection the applicant published the technical datasheet "Palatinol® 7PHP—General Purpose Phthalate" in August 2004.

Plasticizers based on 2-propylheptanol, in particular bis-2-propylheptyl phthalate, have a number of advantageous properties. When compared with other plasticizers using $C_{10}$ alcohols, e.g. diisodecyl phthalate (DIDP)—prepared via trimerization of propene to give nonene mixtures and their subsequent hydroformylation, hydrogenation, and esterification—they also feature lower volatility at relatively high temperatures and better weathering resistance, properties which result in particular interest in plasticizers based on 2-propylheptanol for applications in the cable sector and for interior automobile trim, and also for outdoor use, e.g. for roof coverings and coated tarpaulins. However, other than in niche applications, plasticizers based on 2-propylheptanol have not been able to achieve any great penetration of the market. The main reason for this is the low level of gelling action of plasticizers based on 2-propylheptanol, which makes it more difficult for the user to produce plastified PVC mixtures with these plasticizers.

The gelling action of esters for PVC is mainly characterized via the solution temperature of the ester for PVC, and this can be determined to DIN 53408. The plasticizing action of esters is primarily based on their physical capability to dissolve PVC, in particular at elevated temperatures. The temperature at which the polymer is a clear solution in a particular ester is therefore an important criterion for its usefulness. The lower the solution temperature of the ester for PVC, the better the gelling action. Low solution temperatures permit use of low temperatures during the production and processing of mixtures composed of PVC and ester.

To circumvent these processing problems caused by unfavorable gelling performance of the plasticizer, other esters known as "fast fusers" which have very good gelling performance are added to these plasticizers, particular esters being those of lower alcohols, e.g. dibutyl phthalate or diisobutyl phthalate. Although addition of these fast fusers improves gelling performance, it impairs the properties of the plastic plasticized with this mixture, for example its cold-crack temperature and torsional stiffness, and the evaporation rate of the plasticizer out of the plasticized plastic is increased, leading to undesired phenomena, such as greater fogging and premature embrittlement, during the use of the plastics thus plasticized. Another disadvantage of the fast fusers mentioned is that, because their volatility is relatively high, complicated precautions have to be taken during their processing, to keep their workplace concentration low.

Because the application-related effects described above of plasticizers and of fast fusers are negatively correlated, so that when a mixture composed of plasticizer and fast fuser is used, although the gelling performance of the mixture is improved over that of the pure plasticizer, the advantageous application-related properties of the pure plasticizer are adversely affected to the extent that it is supplemented with a fast fuser, it was an object of the present invention to provide ester mixtures based on the plasticizer alcohol 2-propylheptanol where the gelling performance of the mixtures is improved more than proportionally via addition of esters of another alcohol, in relation to the amount added of the esters of the other alcohol, without more-than-proportional impairment of the other application-related properties of the ester mixtures based on 2-propylheptanol, e.g. cold-crack temperature, torsional stiffness, or volatility from foils. Ideally, the advantageous application-related properties of the ester mixtures based on 2-propylheptanol should be very substantially retained.

SUMMARY OF THE INVENTION

Accordingly, an ester mixture has been found, comprising at least one ester of an aliphatic or aromatic di- or tricarboxylic acid having a $C_{10}$ alcohol component composed of 2-propylheptanol or composed of a $C_{10}$ alcohol mixture composed of 2-propylheptanol and of at least one of the $C_{10}$ alcohols 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol, and comprising at least one ester of an aliphatic or aromatic di- or tricarboxylic acid having a $C_7$ alcohol component composed of n-heptanol or composed of an alcohol mixture composed of n-heptanol with at least one of the $C_7$ alcohols 2-methylhexanol and/or 2-ethylpentanol, where the aliphatic or aromatic di- or tricarboxylic acid has been selected from the group consisting of citric acid, phthalic acid, isophthalic acid, terephthalic acid, and trimellitic acid.

Use of the expression "alcohol component" takes account of the circumstance that the $C_7$ and $C_{10}$ alcohols mentioned are present in esterified form in the inventive $C_7/C_{10}$ ester mixtures.

The $C_{10}$ alcohol component of the inventive $C_7/C_{10}$ ester mixtures—where the "$C_7/C_{10}$" refers to the number of carbon atoms in the alcohol components present therein—derives in essence from 2-propylheptanol or from mixtures of 2-propylheptanol with one or more of its isomers 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol. The abbreviated term "propylheptanol isomers" is used below for these compounds. The presence of other isomers of the 2-propylheptanol component—by way of example, deriving from the alcohols 2-ethyl-2,4-dimethylhexanol, 2-ethyl-2-methylheptanol, and/or 2-ethyl-2,5-dimethylhexanol, which are isomeric with 2-propylheptanol—in the inventive $C_{10}$ alcohol component is possible, but because of the very low rates of formation of the aldehydic precursors of these isomers in the course of the aldol condensation process the amounts of these present in the $C_{10}$ alcohol component, if they are present at all, are only trace amounts, and these are practically irrelevant to the plasticizer properties of the plasticizers comprising the inventive $C_{10}$ alcohol component.

DETAILED DESCRIPTION OF THE INVENTION

Pure 2-propylheptanol can be obtained via aldol condensation of n-valeraldehyde and subsequent hydrogenation of the resultant 2-propylheptanal, for example as in U.S. Pat. No. 2,921,089. However, mixtures of 2-propylheptanol with one or more of the abovementioned propylheptanol isomers are preferably used as starting alcohol for the $C_{10}$ alcohol component of the inventive ester mixtures. The isomer composition in the 2-propylheptanol compositions suitable for the preparation of the inventive ester mixtures can vary, depending on the method of preparation of these compositions and on the nature of the starting material used, and specifically not only in relation to the content of individual isomers in these compositions but also in relation to the presence of certain isomers. Various hydrocarbon sources can be utilized as starting material for the preparation of 2-propylheptanol, examples being 1-butene, 2-butene, raffinate I—an alkane/alkene mixture which is obtained from the $C_4$ cut of a cracker after removal of acetylene and of dienes, and which comprises not only 1- and 2-butene but also considerable amounts of isobutene—or raffinate II, which is obtained from raffinate I via removal of isobutene and whose olefin components comprise only very small proportions of isobutene alongside 1- and 2-butene. Mixtures composed of raffinate I and raffinate II may, of course, also be used as raw material for 2-propylheptanol preparation. These olefins or olefin mixtures may be hydroformylated by methods conventional per se, using cobalt catalysts or rhodium catalysts, the product formed here from 1-butene being a mixture composed of n- and isovaleraldehyde—the term isovaleraldehyde designating for the purposes of this application the compound 2-methylbutanal—and the n/iso ratio of this mixture can vary within relatively wide limits and depends on the catalyst used and the hydroformylation conditions. By way of example, when using a triphenylphosphine-modified homogeneous rhodium catalyst (Rh/TPP) the product formed from 1-butene is n- and isovaleraldehyde in an n/iso ratio which is generally from 10:1 to 20:1, whereas when using rhodium hydroformylation catalysts modified with phosphite ligands, e.g. as in EP-A 155 508 or EP-A 213 639, or with phosphoamidite ligands, e.g. as in WO 02/83695, the product formed is almost exclusively n-valeraldehyde. Whereas the Rh/TPP catalyst system converts 2-butene only very slowly during the hydroformylation process, with the result that most of the 2-butene can be reclaimed from the hydroformylation mixture, hydroformylation of 2-butene is successful with the phosphite-ligand- or phosphoramidite-ligand-modified rhodium catalysts mentioned, the main product formed being n-valeraldehyde. In contrast, isobutene present in the olefinic raw material is hydroformylated by practically all of the catalyst systems, although at varying rate, to give 3-methylbutanal and, as a function of the catalyst, smaller amounts of pivalaldehyde.

The $C_5$ aldehydes obtained as a function of the starting materials and catalysts used, i.e. n-valeraldehyde, optionally mixed with isovaleraldehyde, 3-methylbutanal, and/or pivalaldehyde, may, if desired, be separated entirely or to some extent into the individual components by distillation prior to the aldol condensation process, and there is therefore another possibility here for influencing and controlling the isomeric composition of the $C_{10}$ alcohol component of the inventive ester mixtures. It is also possible to introduce the $C_5$ aldehyde mixture formed during the hydroformylation process into the aldol condensation process without the prior removal of individual isomers. The products from the aldol condensation process, which uses a basic catalyst, such as sodium hydroxide or potassium hydroxide, for example by the methods described in EP-A 366 089, U.S. Pat. No. 4,426,524 or U.S. Pat. No. 5,434,313, is the single condensate 2-propylheptanal if n-valeraldehyde is used, but if a mixture of isomeric $C_5$ aldehydes is used the product is an isomer mixture composed of the products of homoaldol condensation of identical aldehyde molecules and of crossed aldol condensation of different isomers. The aldol condensation process can, of course, be controlled via the specific conversion of individual isomers in such a way that the product formed is mainly or entirely a single aldol condensation isomer. The relevant aldol condensate can then, usually after preliminary, preferably distillative, removal from the reaction mixture, and, if desired, distillative purification, be hydrogenated with conventional hydrogenation catalysts to give the corresponding alcohols or alcohol mixtures, which then serve as starting alcohols for the $C_{10}$ alcohol component during the preparation of the inventive ester mixtures.

Before the resultant 2-propylheptanol or its mixture with the propylheptanol isomers is esterified with an aromatic or aliphatic di- or tricarboxylic acid it may, if desired, also receive admixtures of other $C_{10}$ alcohols, such as n-decanol, methylnonanols, dimethyloctanols, ethyloctanols, trimethylheptanols, methylethylheptanols, butylhexanols, methylpropylhexanols, methylisopropylhexanols, dimethylethylhexanols, tetramethylhexanols, methylbutylpentanols, methylisobutylpentanols, dimethylpropylpentanols, dimethylisopropylpentanols, trimethylethylpentanols, and pentamethylpentanols, but it is preferable to use 2-propylheptanol alone or in a mixture with one or more of the propylheptanol isomers for the $C_{10}$ alcohol component of the inventive ester mixtures.

The content of 2-propylheptanol in the $C_{10}$ alcohols which are used for the preparation of the inventive ester mixtures and which, optionally, also comprise propylheptanol isomers, can be up to 100% by weight, and is generally at least 50% by weight, preferably from 60 to 98% by weight, and particularly preferably from 80 to 95% by weight, in particular from 85 to 95% by weight.

Examples of suitable mixtures of 2-propylheptanol with the propylheptanol isomers comprise those composed of from 60 to 98% by weight of 2-propylheptanol, from 1 to 15% by weight of 2-propyl-4-methylhexanol, and from 0.01 to 20% by weight of 2-propyl-5-methylhexanol, and from 0.01 to 24% by weight of 2-isopropylheptanol, the entirety of the proportions of the individual constituents not exceeding 100% by weight. The proportions of the individual constituents preferably give a total of 100% by weight.

Examples of other suitable mixtures composed of 2-propylheptanol with the propylheptanol isomers comprise those composed of from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol, and from 0.1 to 2% by weight of 2-isopropyl-5-methylhexanol, the entirety of the proportions of the individual constituents not exceeding 100% by weight. The proportions of the individual constituents preferably give a total of 100% by weight.

Preferred mixtures of 2-propylheptanol with the propylheptanol isomers comprise those with from 85 to 95% by weight of 2-propylheptanol, from 6 to 12% by weight of 2-propyl-4-methylhexanol, and from 0.1 to 2% by weight of 2-propyl-5-methylhexanol, and from 0.01 to 1% by weight of 2-isopropylheptanol, the entirety of the proportions of the individual constituents not exceeding 100% by weight. The proportions of the individual constituents preferably give a total of 100% by weight.

Examples of preferred mixtures composed of 2-propylheptanol with the propylheptanol isomers also comprise those composed of from 80 to 92% by weight of 2-propylheptanol, from 6 to 12% by weight of 2-propyl-4-methylhexanol, from 7 to 13% by weight of 2-propyl-5-methylhexanol, from 0.1 to 2% by weight of 2-isopropylheptanol, from 0.1 to 1% by weight of 2-isopropyl-4-methylhexanol, and from 0.1 to 1% by weight of 2-isopropyl-5-methylhexanol, the entirety of the proportions of the individual constituents not exceeding 100% by weight. The proportions of the individual constituents preferably give a total of 100% by weight.

The composition of the $C_{10}$ alcohol component in the inventive ester mixtures is practically the same as the composition of the propylheptanol isomer mixtures used during the esterification process for their preparation.

Contaminants which may remain present, deriving from the preparation process, in the mixtures composed of 2-propylheptanol with the propylheptanol isomers are traces of n-pentanol, 2-methylbutanol, and/or 3-methylbutanol. The contents of these alcohols are generally in each case at most 0.5%.

The $C_7$ alcohol component of the inventive ester mixture derives in essence from n-heptanol or from an alcohol mixture composed of n-heptanol with at least one of the $C_7$ alcohols 2-methylhexanol and/or 2-ethylpentanol. The abbreviated term "n-heptanol isomers" is used below for these compounds. The presence of a total amount of up to 15% by weight, preferably up to 10% by weight, of other isomers of the n-heptanol component—by way of example, derived from 3-methylhexanol, from 4-methylhexanol, from 5-methylhexanol, from 3,4-dimethylpentanol, and/or from 2-ethyl-3-methylbutanol—in the $C_7$ alcohol component to be used according to the invention is possible, but because the amounts present of the individual compounds in the $C_7$ alcohol component are small—entrained via olefinic contaminants in the 1-hexene starting material as a function of the preparation of that starting material—they are generally of subordinate importance for the plasticizer properties of the plasticizers comprising the inventive $C_7$ alcohol component.

Heptanol and its mixtures with n-heptanol isomers may be prepared in various ways, e.g. starting from 1-hexene via its hydroformylation to give n-heptanal and, as a function of the hydroformylation catalyst used, the aldehydes isomeric therewith: 2-methylhexanal and/or 2-ethylpentanal, the latter being formed via a double-bond isomerization side-reaction prior to the hydroformylation reaction, and subsequent hydrogenation of these aldehydes to give the corresponding alcohols. The 1-hexene used as starting material is commercially available from various sources, for example by way of ethene oligomerization by means of the Ziegler catalysts, the SHOP process, or the Fischer-Tropsch process. Kirk-Othmer; Encyclopedia of Chemical Technology; Vol. 17; pp. 843-854; John Wiley & Sons; New York 1996 gives a summary of these processes. The hydroformylation catalysts used may be the same as those mentioned above in the context of the hydroformylation of butenes in the course of 2-propylheptanol preparation, preference being given to the use of rhodium hydroformylation catalysts. Practically any of the familiar hydrogenation catalysts is suitable for the hydrogenation of the aldehyde group to give the alcohol.

The content of n-heptanol in the $C_7$ alcohols used for preparation of the inventive ester mixtures can be up to 100% by weight and is generally at least 30% by weight, preferably from 50 to 99% by weight, particularly preferably from 60 to 98% by weight.

Examples of suitable mixtures of n-heptanol with the heptanol isomers comprise those composed of from 30 to 99% by weight of n-heptanol, from 1 to 30% by weight of 2-methylhexanol, and/or from 0.01 to 20% by weight of 2-ethylpentanol, the entirety of the proportions of the individual constituents not exceeding 100% by weight.

Examples of other suitable mixtures of n-heptanol with the heptanol isomers comprise those composed of from 70 to 99% by weight of n-heptanol, from 1 to 20% by weight of 2-methylhexanol, and from 0.01 to 2% by weight of 2-ethylpentanol, the entirety of the proportions of the individual constituents not exceeding 100% by weight.

Examples of preferred mixtures of n-heptanol with the heptanol isomers comprise those composed of from 50 to 80% by weight of n-heptanol, from 10 to 25% by weight of 2-methylhexanol, and/or from 2 to 10% by weight of 2-ethylpentanol, the entirety of the proportions of the individual constituents not exceeding 100% by weight.

Examples of further preferred mixtures of n-heptanol with the heptanol isomers comprise those composed of from 85 to 98% by weight of n-heptanol, from 2 to 10% by weight of 2-methylhexanol, and from 0.01 to 1% by weight of 2-ethylpentanol, the entirety of the proportions of the individual constituents not exceeding 100% by weight.

If no other isomeric heptanols are present in the mixtures of n-heptanol with the heptanol isomers, the proportions of the individual constituents of the heptanol mixtures mentioned above by way of example give a total of 100% by weight.

The composition of the $C_7$ alcohol component in the inventive ester mixtures corresponds to the composition of the $C_7$ alcohol mixtures used during the esterification process for their preparation.

The aromatic or aliphatic di- or tricarboxylic acid component of the inventive ester mixtures may be citric acid, phthalic acid, isophthalic acid, terephthalic acid, or trimellitic acid. In general, the inventive ester mixtures generally comprise only one of the specified di- or tricarboxylic acids as carboxylic acid component. The esters of phthalic acid are particularly preferred. All of these di- and tricarboxylic acids, and also the anhydrides of phthalic acid and of trimellitic acid, are produced industrially and are commercially available.

The $C_7$ and $C_{10}$ alcohol component in the inventive ester mixtures may A) have random distribution in the ester mixture, or B) the ester mixtures may be composed of mixed esters which are in essence uniform, in which, for example, one carboxy group has been esterified with the $C_7$ alcohol component, and the other carboxy group(s) has/have been esterified with the $C_{10}$ alcohol component, or vice versa, or, preferably, C) the di- or triesters of the di- or, respectively, tricarboxylic acid with the $C_{10}$ alcohol component, and the di- or, respectively, triesters of the di- or, respectively, tricarboxylic acid with the $C_7$ alcohol component may be present alongside one another in the ester mixture.

To prepare the inventive ester mixtures of type A, a mixture composed of the $C_7$ and $C_{10}$ alcohols in the desired $C_7/C_{10}$ ratio by weight can be esterified in a conventional manner, for example with proton-acid catalysis, preferably with sulfuric-acid catalysis, or particularly preferably with amphoteric titanium-tetraalcoholate or zirconium-tetraalcoholate, or tin-tetraalcoholate catalysis, in stoichiometric excess, with the relevant di- or tricarboxylic acid or its anhydride at temperatures of from 80 to 250° C., preferably from 100 to 240° C., in particular at temperatures of from 150 to 230° C., at atmospheric pressure or preferably at reduced pressure, and generally with distillative removal of the water of reaction in order to take the esterification reaction to complete conversion. After neutralization or hydrolysis and removal of the esterification catalyst, for example in phase separators or via filtration or centrifuging, the resultant ester mixtures can be isolated from contaminants, such as water or unconverted alcohol, for example via distillation. Towae et al. in Ullmann's Encyclopedia of Industrial Chemistry, 5th Ed., Vol. A20, pp. 193-196, VCH Publishers, Weinheim 1992 give a detailed description of the conduct of this esterification process for the preparation of phthalic esters, and in principle this is also analogously applicable to the preparation of other di- or tricarboxylic esters. By way of example, WO 02/038531, U.S. Pat. No. 6,310,235 B1, U.S. Pat. No. 5,324,853, DE-A 2 612 355 (Derwent Abstract No. DW 77-72638 Y), or DE-A 1 945 359 (Derwent Abstract Nr. DW 73-27151 U) also gives detailed descriptions of the conduct of esterification processes.

There are various ways of preparing the inventive ester mixtures of type B. If a di- or tricarboxylic acid is used as starting material, this can be converted in such a way, via addition of a stoichiometric amount of the relevant $C_7$ or $C_{10}$ alcohols, as to form mainly the monoester. This can, if desired, after work-up of the reaction mixture be isolated from unconverted di- or tricarboxylic acid or di- or triesters by distillation and then analogously esterified with the other alcohol component, so that the products formed are the desired $C_7/C_{10}$ diesters, di-$C_7$ mono-$C_{10}$ triesters, or di-$C_{10}$ mono-$C_7$ triesters. The catalysts and reaction conditions which can be used here are practically the same as those for the preparation of the ester mixtures of type A.

If an anhydride is used as starting material, for example phthalic anhydride or trimellitic anhydride, monoester formation takes place with the $C_7$ or $C_{10}$ alcohol component even in the absence of a catalyst via addition of the alcohol to the anhydride group, and even at temperatures below 160° C., for example at from 100 to 150° C. The resultant monoesters can then be esterified to completion after addition of the catalyst, for example of the titanium-alcoholate catalyst, and of the other alcohol component, and after increasing the temperature of the reaction mixture to 160-250° C. and removing the water of reaction.

The operating methods described in U.S. Pat. No. 5,324, 853 and U.S. Pat. No. 6,310,235 B1 can be applied analogously to the preparation of these mixed $C_7/C_{10}$ esters.

Particular preference is given to the inventive ester mixtures of type C, in which di- or, respectively, triesters of the relevant di- or, respectively, tricarboxylic acid with the $C_7$ alcohol component and the di- or, respectively, triesters of the relevant di- or tricarboxylic acid with the $C_{10}$ alcohol component are present alongside one another. These ester mixtures can be prepared in a manner conventional per se, by fully esterifying the relevant di- or tricarboxylic acid or anhydride thereof in separate reactions with the $C_7$ or, respectively, $C_{10}$ alcohols, and, after conventional work-up, mixing the resultant $C_7$ or, respectively, $C_{10}$ di- or triesters in the desired ratio with one another. In this case, too, the esterification may take place within the ranges of temperature and pressure stated above via proton catalysis, for example by means of sulfuric acid, or by means of amphoteric catalysts, such as titanium-tetraalcoholate, zirconium-tetraalcoholate, or tin-tetraalcoholate catalysts. By way of example, the methods described in WO 02/38531, U.S. Pat. No. 6,310,235B1, U.S. Pat. No. 5,324,853, DE-A 2 612 355 (Derwent Abstract No. DW 77-72638 Y), or DE-A 1 945 359 (Derwent Abstract No. DW 73-27151U) may be applied to the preparation of these esters. Once the $C_7$ or, respectively, $C_{10}$ di- or triesters of the relevant di- or tricarboxylic acid have been isolated, these can be mixed with one another in the desired quantitative proportions to give tailored products for the intended application as plasticizer.

As a function of the desired usage properties of the PVC compositions plasticized with the inventive ester mixture, it can be advantageous to vary the proportion by weight of the $C_{10}$ and the $C_7$ alcohol component during the esterification process with the relevant di- or tricarboxylic acid in such a way that the $C_{10}$ and the $C_7$ alcohol component in the inventive ester mixtures are present esterified in different $C_7/C_{10}$ ratios by weight with the relevant di- or tricarboxylic acid. For example, the ratio by weight of the $C_7$ alcohol component with respect to the $C_{10}$ alcohol component in the inventive ester mixtures can be from 5:95 to 95:5, preferably from 20:80 to 80:20, particularly preferably from 25:75 to 75:25. The proportions of the $C_{10}$ and of the $C_7$ alcohol component, and also the individual composition of these components, can be analyzed in the inventive ester mixture in a manner familiar to the person skilled in the art, via saponification of the ester mixture with aqueous alkali metal hydroxide, for example sodium hydroxide solution or potassium hydroxide solution, extraction of the alcohols liberated from the saponification mixture, for example by means of diethyl ether, and gas-chromatographic separation of the alcohols, advantageously after preliminary derivatization, for example by means of N-methyl-N-(trimethylsilyl)trifluoroacetamide to give the corresponding trimethylsilyl ethers.

As a function of the composition, the density of the inventive ester mixtures is generally from 0.90 g/cm³ to 1.05 g/cm³ at 25° C., preferably from 0.96 g/cm³ to 0.99 g/cm³, and particularly preferably from 0.97 g/cm³ to 0.98 g/cm³, measured to DIN 51757 or ASTM D4052, their dynamic viscosity generally being from 10 mPa*s to 200 mPa*s at 20° C., preferably from 35 mPa*s to 130 mPa*s, and particularly preferably from 60 mPa*s to 80 mPa*s, measured to DIN 51562 or ASTM D445.

As a function of the composition of the inventive ester mixtures, the solution temperature of the inventive ester mixtures for PVC, determined to DIN 53408, is in the range from 110 to 145° C., preferably in the range from 115 to 140° C., particularly preferably in the range from 120 to 130° C., in particular from 125 to 130° C.

The inventive ester mixtures have excellent suitability for plasticizing PVC. Accordingly, the present invention also provides compositions composed of polyvinyl chloride comprising an amount which is generally from 1 to 100 phr of an inventive ester mixture. The conventional formulation unit "phr" for polymer compositions is the abbreviation for "parts per hundred resin" and means that the amounts of additive weighed-out, measured and stated are not percentage content in the entire composition, but parts by weight for every one hundred parts by weight of polymer. By way of example, if the PVC:plasticizer ratio by weight in which the inventive ester mixture is present in the PVC/plasticizer mixture is 80:20, the ester mixture content is 25 phr, because 20 parts represent 25% of 80 parts.

Polyvinylchloride, produced via homopolymerization of vinyl chloride, can be prepared industrially in various ways, examples being suspension polymerization, microsuspension polymerization, emulsion polymerization, and bulk polymerization. The K value, which characterizes the molar mass of the PVC and is determined to DIN 53726, can be in the range from 57 to 90, preferably in the range from 61 to 85, and particularly preferably in the range from 64 to 75 for PVC grades used according to the invention. Kirk-Othmer, Encyclopedia of Chemical Technology, 4th Ed., Vol. 24, pp. 1017-1047, gives an overview of the properties, preparation, and use of PVC, and also describes the relationship between K value, number-average molecular weight, weight-average molecular weight, and the inherent and relative viscosity of the PVC measured to ASTM L1234.

The PVC contents of the inventive compositions may generally be from 20 to 99% by weight, preferably from 30 to 90% by weight, particularly preferably from 35 to 80% by weight, and in particular from 40 to 75% by weight, based in each case on the total weight of the PVC composition, i.e. including all of the constituents of the PVC composition.

The content of the inventive ester mixture—stated in phr—in the inventive PVC compositions may generally be from 1 to 100 phr, preferably from 10 to 90 phr, and particularly preferably from 30 to 80 phr.

Materials other than PVC and the inventive ester mixtures which may be present in the inventive PVC compositions are one or more other additives usually present in PVC mixtures as a function of their intended use in order to improve their mechanical, chemical, and processing properties. Merely by way of example, mention may be made in this context of stabilizers, lubricants, fillers, pigments, flame retardants, light stabilizers, blowing agents, polymeric processing aids, impact modifiers, optical brighteners, antistatic agents, and biostabilizers.

Merely for the purposes of illustration of the inventive PVC compositions, some of these additives and their function are described by way of example below, but these descriptions do not restrict the inventive PVC compositions.

Stabilizers neutralize, by way of example, the hydrochloric acid eliminated from PVC during and/or after processing.

Stabilizers which may be used are any of the conventional stabilizers in solid or liquid form, examples being conventional Ca/Zn, Ba/Zn, Pb, or Sn stabilizers, and also acid-binding phyllosilicates, such as hydrotalcite. Preference is given to Ba/Zn stabilizers, tribasic lead sulfate (3 $PbO*PbSO_4*H_2O$), and lead phosphite, and tribasic lead sulfate and lead phosphite are particularly preferred.

The content of stabilizers in the inventive PVC compositions may be from 0.05 to 7 phr, preferably from 0.1 to 5 phr, particularly preferably from 0.2 to 4 phr, and in particular from 0.3 to 2 phr.

Lubricants are intended to act between PVC particles and to counteract frictional forces during mixing, plastification, and forming.

Lubricants which may be present in the inventive PVC compositions are any of the conventional lubricants for PVC processing. Examples of those which may be used are hydrocarbons, such as oils, paraffins, and polyethylene waxes, fatty alcohols having from 6 to 20 carbon atoms, ketones, carboxylic acids, such as fatty acids and montanic acid, oxidized polyethylene wax, metal carboxylates, carboxamides, and also carboxylic esters, such as those with the following alcohols: ethanol, fatty alcohols, glycerol, ethanediol, and pentaerythritol, and with long-chain carboxylic acids as acid component. It is preferable to use lead stearate.

The content of lubricant in the inventive PVC compositions may be from 0.01 to 10 phr, preferably from 0.05 to 5 phr, particularly preferably from 0.1 to 3 phr, and in particular from 0.2 to 2 phr.

Fillers primarily affect resistance to pressure, to tension, and to flexure, and also affect the hardness and the heat resistance of plasticized polyvinyl chloride, the effect being favorable.

The inventive PVC compositions may receive admixtures of fillers, such as carbon black and other inorganic fillers, e.g. naturally occurring calcium carbonates, such as chalk, limestone, and marble, synthetic calcium carbonates, dolomite, silicates, silica, sand, diatomaceous earth, and aluminum silicates, such as kaolin, mica, and feldspar. The fillers used preferably comprise calcium carbonates, chalk, dolomite, kaolin, silicates, talc, or carbon black, chalk being particularly preferred.

The content of fillers in the inventive mixtures may be from 0.01 to 80 phr, preferably from 1 to 60 phr, particularly preferably from 5 to 50 phr, and in particular from 15 to 40 phr.

The inventive PVC compositions may also comprise pigments in order to adapt the resultant product to various possible uses.

Either inorganic pigments or else organic pigments may be used for this purpose. Examples of inorganic pigments which may be used are cadmium pigments, such as CdS, cobalt pigments, such as $CoO/Al_2O_3$, and chromium pigments, such as $Cr_2O_3$. Examples of organic pigments which may be used are monoazo pigments, condensed azo pigments, azomethine pigments, anthraquinone pigments, quinacridones, phthalocyanine pigments, dioxazine pigments, such as C.I. Pigment Violet 23 and Aniline Black (C.I. Pigment Black 1).

The content of pigments in the inventive PVC compositions may be from 0.01 to 10 phr, preferably from 0.05 to 5 phr, particularly preferably from 0.1 to 3 phr, and in particular from 0.5 to 2 phr.

In order to reduce flammability and smoke generation during combustion, flame retardants may also be added to the inventive PVC compositions.

Examples of flame retardants which may be used are antimony trioxide, phosphoric esters, chloroparaffin, aluminum hydroxide, boron compounds, molybdenum trioxide, ferrocene, calcium carbonate, or magnesium carbonate. It is preferable to use antimony trioxide or phosphoric esters, particular preference being given to phosphoric esters, in particular bisphenyl cresyl phosphate, diphenyl octyl phosphate or tricresyl phosphate.

The content of flame retardants in the inventive PVC compositions may be from 0.01 to 10 phr, preferably from 0.1 to 8 phr, particularly preferably from 0.2 to 5 phr, and in particular from 0.5 to 3 phr.

In order to protect items produced from the inventive PVC compositions, from superficial damage by light, light stabilizers may also be added to these PVC compositions.

Examples of those which may be used for this purpose are hydroxybenzophenones, hydroxyphenylbenzotriazoles, or cyanophenylacrylates. Preference is given to cyanophenylacrylates, particularly preferably 2-ethylhexyl 2-cyano-3,3-diphenylacrylate.

The amount of light stabilizers which may be present in the inventive PVC compositions is from 0.01 to 7 phr, preferably from 0.1 to 5 phr, particularly preferably from 0.2 to 4 phr, and in particular from 0.5 to 3 phr.

The usual method of preparation of the inventive PVC compositions is mixing of the individual components at elevated temperatures, with stirring. L. Meier in R. Gächter, H. Müller (Ed.); Plastics Additives Handbook, 3rd Ed., Chapters 5.4.3, 5.4.4, Hanser Publishers, Munich 1990 gives, by way of example, a general description of the preparation of mixtures composed of polyvinyl chlorides, esters, and other additives.

The inventive PVC compositions are suitable, by way of example, for the production of foils, such as self-adhesive foils, automotive foils, furniture foils, stationery foils, agricultural foils, food foils (cling film), roof sheeting, oil tank liner foils, reservoir liner foils, swimming pool liner foils, construction foils, raincoats, swing doors, shower curtains, inflatable boats, flotation belts, and also foils for medical applications, such as blood bags or infusion bags.

The inventive PVC compositions are also suitable for the production of cables, for example of wiring cables, power cables, communications cables, coiled cord, computer cables, and automotive cables.

The inventive PVC compositions are also suitable for the production of coatings, for example for synthetic leather (applications in automobiles and in bag manufacture), truck tarpaulins, tenting, table cloths, protective clothing, vinyl wallcoverings, and conveyor belts.

The inventive PVC compositions are moreover suitable for the production of floorcoverings, for example of foamed floorcoverings (cushion vinyl), heterogeneous compact coverings, homogeneous compact coverings, and for coatings on carpeting, and for laminates.

The inventive mixtures composed of PVC and of the inventive ester mixtures are also suitable for the production of profiles, e.g. industrial hoses, garden hoses, seals (e.g. for refrigerators), medical tubing, staircase handrails, and window profiles.

The inventive PVC compositions are also particularly suitable for the production of shoes (boots, sandals), soles, toys, gloves (industrial, medical), closure caps, and erasers.

Possible means of production of these finished items from the inventive mixtures are thermoforming, calendering, extrusion, coating, casting, dip-coating, rotor molding, or injection molding. D. H. Morton-Jones, Polymer Processing, Chapman and Hall, London 1989, describes by way of example details of these processing methods.

The inventive PVC compositions are particularly suitable for the production of pastes (plastisols, organosols, or plastigels) which are processed by dip-coating, spreading, casting, rotation molding, centrifugal casting, or injection molding, or else by rotary screen printing, to give end products. Examples of end products which are produced by way of this process are balls, dolls, traffic cones, truck tarpaulin materials, flat tarpaulins, tenting, bag-manufacture products, ventilation ducts, synthetic leather, floor- and wallcoverings, wallpapers (including those foamed by mechanical or chemical means), cladding, protective gloves, protective clothing, and protective coverings on metallic substrates, other examples being folding bellows, underbody protection for motor vehicles, and seals for twist-off closures, crown caps, and screw closures.

The inventive examples below give further illustration of the invention, which is not, however, restricted to these examples.

INVENTIVE EXAMPLE 1

Preparation of an Inventive Ester Mixture a) Preparation of a $C_7$ Phthalic Ester Mixture A mixture of alcohols having 7 carbon atoms (2.4 mol; 1.2-fold stoichiometric excess), comprising 66.0% by weight of n-heptanol, 18.1% by weight of 2-methylhexanol, 1.5% by weight of 3-methylhexanol, 0.8% by weight of 4-methylhexanol, 1.0% by weight of 3,4-dimethylpentanol, 6.6% by weight of 2-ethylpentanol, and 5.7% by weight of 2-ethyl-3-methylbutanol, was reacted with phthalic anhydride (1.0 mol) in the presence of isopropyl butyl titanate (0.001 mol) as catalyst in an autoclave into which $N_2$ was bubbled, with stirring, the reaction temperature being 230° C. The water of reaction formed was progressively removed from the reaction mixture with the $N_2$ stream. The reaction time was 180 min. Excess alcohols were then removed by distillation at a pressure of 50 mbar. The crude $C_7$ phthalic ester mixture was neutralized with 0.5% strength sodium hydroxide solution via stirring at 80° C. A two-phase mixture formed, with an upper organic phase and a lower aqueous phase (waste liquor with hydrolyzed catalyst). The aqueous phase was removed, and the organic phase was washed twice with $H_2O$. For further purification, the neutralized and washed $C_7$ phthalic ester mixture was steam-stripped at 180° C. in vacuo at 50 mbar. The resultant purified $C_7$ phthalic ester mixture was then dried at 150° C./50 mbar by passing a stream of $N_2$ through the material, then mixed with activated charcoal and isolated by filtration through a suction funnel with Supra-Theorit 5 filtration aid (fibrous filtration aid based on kieselguhr and cellulose; producer: Seitz Schenk Filtersystems GmbH, Bad Kreuznach, Germany) at 80° C., using reduced pressure.

b) Preparation of a $C_{10}$ Phthalic Ester Mixture

A mixture of alcohols having 10 carbon atoms (2.4 mol; 1.2-fold stoichiometric excess), comprising 89.49% by weight of 2-propylheptanol, 10.47% by weight of 2-propyl-4-methylhexanol, and 0.04% by weight of 2-propyl-5-methylhexanol was reacted with phthalic anhydride (1.0 mol) in the presence of isopropyl butyl titanate (0.001 mol) as catalyst in an autoclave into which $N_2$ was bubbled, with stirring, the reaction temperature being 230° C. The water of reaction formed was progressively removed from the reaction mixture with the $N_2$ stream. The reaction time was 180 min. Excess alcohols were then removed by distillation at a pressure of 50 mbar. The crude $C_{10}$ phthalic ester mixture was neutralized with 0.5% strength sodium hydroxide solution via stirring at 80° C. A two-phase mixture formed, with an upper organic phase and a lower aqueous phase (waste liquor with hydrolyzed catalyst). The aqueous phase was removed, and the organic phase was washed twice with $H_2O$. For further purification, the neutralized and washed $C_{10}$ phthalic ester mixture was steam-stripped at 180° C. at a pressure of 50 mbar. The resultant purified $C_{10}$ phthalic ester mixture was then dried at 150° C./50 mbar by passing a stream of $N_2$ through the material, then mixed with activated charcoal and isolated by filtration through a suction funnel with Supra-Theorit filtration aid at a temperature of 80° C., using reduced pressure.

c) Preparation of an Inventive $C_7/C_{10}$ Phthalic Ester Mixture

The $C_7$ phthalic ester mixture from inventive example 1a and the $C_{10}$ phthalic ester mixture from inventive example 1b were mixed in a ratio by weight of 1:1, thus giving a $C_7/C_{10}$ phthalic ester mixture composed of 50% by weight of $C_7$ phthalic ester mixture and 50% by weight of $C_{10}$ phthalic ester mixture.

The density of the resultant inventive $C_7/C_{10}$ phthalic ester mixture at 25° C. (DIN 51757 or ASTM D4052) is 0.976 g/cm$^3$, and its dynamic viscosity at 20° C. (DIN 51562 or ASTM D445) is 69 mPa*s.

D) Determination of the Solution Temperature of the Inventive $C_7/C_{10}$ Phthalic Ester Mixture The PVC-solution temperature of the $C_7$ phthalic ester mixture from inventive example 1a) and of the inventive $C_7/C_{10}$ phthalic ester mixture from inventive example 1c) was determined as specified by DIN 53408. The values are listed in table 1.

COMPARATIVE EXAMPLE 1

For comparison, by analogy with inventive example 1b, 2-propylheptanol and phthalic anhydride were used to prepare a di(2-propylheptyl)phthalate as in U.S. Pat. No. 2,921,089, and the solution temperature was determined as stated in inventive example 1d. This is also listed in table 1.

INVENTIVE EXAMPLE 2

Preparation of an Inventive Mixture Composed of PVC and of the $C_7/C_{10}$ Phthalic Ester Mixture from Inventive Example 1

100 parts by weight of GEON 103 EPF76 PVC powder (producer: PolyOne Corporation; Cleveland, Ohio) with K value 65, 40 parts by weight of the inventive $C_7/C_{10}$ phthalic ester mixture from inventive example 1, 2 parts by weight of lead phosphite, and 1 part of lead stearate were mixed at room temperature, using a manual mixer. The mixture was then plastified on steam-heated laboratory mixing rolls at a temperature of 170° C. and processed to give a milled sheet. After cooling, the resultant milled sheet was then pressed at a temperature of 180° C. and a pressure of 220 bar to give a plasticized PVC foil.

The resultant plasticized PVC foil is composed of 69.9% by weight of PVC, 28.0% by weight of $C_7/C_{10}$ phthalic ester mixture, 1.4% by weight of lead phosphite, and 0.7% by weight of lead stearate.

This plasticized PVC foil was used to determine cold-crack temperature (to ASTM method D746), torsional stiffness (to ASTM method D1043), and volatile loss from the foil (to ASTM method D1203). The results are given in table 1.

COMPARATIVE EXAMPLE 2

Preparation of a Mixture Composed of PVC and of a di(2-propylheptyl)phthalate as in U.S. Pat. No. 2,921,089 from Comparative Example 1

By analogy with inventive example 2, a plasticized PVC foil was produced, composed of 69.9% by weight of PVC, 28.0% by weight of di(2-propylheptyl)phthalate, 1.4% by weight of lead phosphite, and 0.7% by weight of lead stearate.

This plasticized PVC foil was used to determine cold-crack temperature (to ASTM method D746), torsional stiffness (to ASTM method D1043), and volatile loss from the foil (to ASTM method D1203). The results are given in table 1.

COMPARATIVE EXAMPLE 3

Preparation of a Mixture Composed of PVC and of the $C_7$ Phthalic Ester Mixture from Inventive Example 1a By analogy with inventive example 2, a plasticized PVC foil was produced, composed of 69.9% by weight of PVC, 28.0% by weight of $C_7$ phthalic ester mixture, 1.4% by weight of lead phosphite, and 0.7% by weight of lead stearate.

This plasticized PVC foil was used to determine cold-crack temperature (to ASTM method D746), torsional stiffness (to ASTM method D1043), and volatile loss from the foil (to ASTM method D1203). The results are given in table 1.

from the film are at a comparable level in plasticized PVC foils produced using these esters.

The results in table 1 also show that the inventive $C_7/C_{10}$ phthalic ester mixtures contrast with di(2-propylheptyl)phthalate as in U.S. Pat. No. 2,921,089 and with the $C_7$ phthalic ester mixture as in inventive example 1a in their synergistic effect in relation to PVC solution temperature. The PVC solution temperature of the inventive $C_7/C_{10}$ phthalic ester mixtures is markedly lower at 126° C. than the calculated average of the solution temperature for a 1:1 mixture composed of the di(2-propylheptyl)phthalate as in U.S. Pat. No. 2,921,089 and of the $C_7$ phthalic ester mixture as in inventive example 1a, which would be 131° C. ((115+146)/2=131).

What is claimed is:

1. An ester mixture comprising at least one ester of an aliphatic or aromatic di- or tricarboxylic acid having a $C_{10}$ alcohol component composed of 2-propylheptanol or composed of a $C_{10}$ alcohol mixture composed of 2-propylheptanol and of at least one of the $C_{10}$ alcohols selected from the group consisting of 2-propyl-4-methylhexanol, 2-propyl-5-methylhexanol, 2-isopropylheptanol, 2-isopropyl-4-methylhexanol, 2-isopropyl-5-methylhexanol, and 2-propyl-4,4-dimethylpentanol, and comprising at least one ester of an aliphatic or aromatic di- or tricarboxylic acid having a $C_7$ alcohol component composed of n-heptanol or composed of an alcohol mixture composed of n-heptanol and at least one of the $C_7$ alcohols selected from the group consisting of 2-methylhexanol and 2-ethylpentanol, wherein the aliphatic or aromatic di- or tricarboxylic acid is selected from the group consisting of citric acid, phthalic acid, isophthalic acid, terephthalic acid, and trimellitic acid.

2. The ester mixture according to claim 1, comprising at least one diester of an aliphatic or aromatic dicarboxylic acid or at least one triester of an aliphatic or aromatic tricarboxylic acid having a $C_{10}$ alcohol component composed of 2-propylheptanol or composed of a $C_{10}$ alcohol mixture composed of 2-propylheptanol and of at least one of the $C_{10}$ alcohols selected from the group consisting of 2-propyl-4-methylhexanol, 2-propyl-5-methylhexanol, 2-isopropylhep-

TABLE 1

|  | Inventive $C_7/C_{10}$ phthalic ester mixture from inventive example 1 | Di(2-propylheptyl) phthalate as in US 2 921 089 from comparative example 1 | $C_7$ Phthalic ester mixture from inventive example 1a |
|---|---|---|---|
| PVC solution temperature of ester in ° C. (DIN 53408) | 126 | 146 | 115 |
| Cold-crack temperature of foil in ° C. (ASTM method D746) | −22 | −21 | −24 |
| Torsional stiffness of foil in ° C. (ASTM method D1043) | −9 | −8 | −11 |
| Volatile loss from foil at 70° C./24 h in % by weight (ASTM method D1203) | 0.5 | 0.2 | 0.8 |

The results in table 1 show that the inventive $C_7/C_{10}$ phthalic ester mixture has a markedly lower PVC solution temperature at 126° C. than the di(2-propylheptyl) phthalate as in U.S. Pat. No. 2,921,089 at 146° C. At the same time, cold-crack temperature, torsional stiffness, and volatile loss tanol, 2-isopropyl-4-methylhexanol, 2-isopropyl-5-methylhexanol, and 2-propyl-4,4-dimethylpentanol, and comprising at least one diester of an aliphatic or aromatic dicarboxylic acid or at least one triester of an aliphatic or aromatic tricarboxylic acid having a $C_7$ alcohol component composed of n-heptanol or composed of an alcohol mixture composed of n-heptanol and at least one of the $C_7$ alcohols selected from the group consisting of 2-methylhexanol and 2-ethylpentanol.

3. The ester mixture according to claim 1, in which the esters of the $C_{10}$ alcohol component are present in a ratio by weight of from about 5:95 to about 95:5 with respect to the esters of the $C_7$ alcohol component.

4. The ester mixture according to claim 1 comprising esters of phthalic acid.

5. The ester mixture according to claim 1, in which at least 50% by weight of the $C_{10}$ alcohol component derives from 2-propylheptanol.

6. The ester mixture according to claim 1, in which from 60 to 98% by weight of the $C_{10}$ alcohol component derives from 2-propylheptanol, from 1 to 15% by weight of that component derives from 2-propyl-4-methylhexanol, from 0.01 to 20% by weight of that component derives from 2-propyl-5-methylhexanol, from 0.01 to 4% by weight of that component derives from 2-isopropylheptanol, from 0 to 2% by weight of that component derives from 2-isopropyl-4-methylhexanol, and from 0 to 2% by weight of that component derives from 2-isopropyl-5-methylhexanol, the entirety of the individual constituents not exceeding 100% by weight.

7. The ester mixture according to claim 1, in which at least 30% by weight of the $C_7$ alcohol component derives from n-heptanol.

8. The ester mixture according to claim 1, in which from 30 to 99% by weight of the $C_7$ alcohol component derives from n-heptanol, from 1 to 30% by weight of that component derives from 4-methylhexanol, and from 0.01 to 20% by weight of that component derives from 2-ethylpentanol, the entirety of the individual constituents not exceeding 100% by weight.

9. A composition comprising (1) polyvinyl chloride (PVC) and (2) an ester mixture in an amount from about 1 to about 100 parts per hundred parts by weight of PVC, said ester mixture comprises at least one ester of an aliphatic or aromatic di- or tricarboxylic acid having a $C_{10}$ alcohol component composed of 2-propylheptanol or composed of a $C_{10}$ alcohol mixture composed of 2-propylheptanol and of at least one of the $C_{10}$ alcohols selected from the group consisting of 2-propyl-4-methylhexanol, 2-propyl-5-methylhexanol, 2-isopropylheptanol, 2-isopropyl-4-methylhexanol, 2-isopropyl-5-methylhexanol, and 2-propyl-4,4-dimethylpentanol, and comprising at least one ester of an aliphatic or aromatic di- or tricarboxylic acid having a $C_7$ alcohol component composed of n-heptanol or composed of an alcohol mixture composed of n-heptanol and at least one of the $C_7$ alcohols selected from the group consisting of 2-methylhexanol and 2-ethylpentanol, wherein the aliphatic or aromatic di- or tricarboxylic acid is selected from the group consisting of citric acid, phthalic acid, isophthalic acid, terephthalic acid, and trimellitic acid.

\* \* \* \* \*